(12) United States Patent
Fontaine et al.

(10) Patent No.: US 8,529,966 B2
(45) Date of Patent: Sep. 10, 2013

(54) BURN TREATMENT COMPOSITION AND METHOD

(75) Inventors: Wanda Fontaine, Bloomfield, NJ (US); Diane Madfes, Greenwich, CT (US); Irwin Palefsky, Plainview, NY (US); Ni'kita Wilson, Union, NJ (US)

(73) Assignee: Healing Skin LLC, New York, NY (US)

( * ) Notice: Subject to any disclaimer, the term of this patent is extended or adjusted under 35 U.S.C. 154(b) by 73 days.

(21) Appl. No.: 12/687,864

(22) Filed: Jan. 14, 2010

(65) Prior Publication Data

US 2010/0112103 A1 May 6, 2010

Related U.S. Application Data

(62) Division of application No. 12/035,438, filed on Feb. 22, 2008, now abandoned.

(60) Provisional application No. 60/891,158, filed on Feb. 22, 2007, provisional application No. 60/947,478, filed on Jul. 2, 2007.

(51) Int. Cl.
*A61K 36/00* (2006.01)
*A61K 36/886* (2006.01)

(52) U.S. Cl.
USPC .......................... 424/725; 424/744; 424/764

(58) Field of Classification Search
None
See application file for complete search history.

(56) References Cited

U.S. PATENT DOCUMENTS 6,562,326 B1 * 5/2003 Miller ....................... 424/70.19
2007/0093161 A1 * 4/2007 Eede et al. .................. 442/149

FOREIGN PATENT DOCUMENTS

| AU | 9177154 A | * | 12/1991 |
| WO | WO 02098404 A1 | * | 12/2002 |
| WO | WO 2007/087583 A2 | * | 8/2007 |

* cited by examiner

*Primary Examiner* — Qiuwen Mi

(57) ABSTRACT

The invention is directed to a method for treating topical burns with compositions comprising a silicone containing compound, a Vitamin E compound and a local anesthetic.

20 Claims, No Drawings

BURN TREATMENT COMPOSITION AND METHOD

PRIORITY CLAIM

This application claims priority under 35 USC §119(e) from application Ser. No. 60/891,158, filed Feb. 22, 2007 and application Ser. No. 60/947,478 filed Jul. 2, 2007, the contents of each (appln. Ser. Nos. 60/891,158 and 60/947,478) of which are incorporated by reference in their entireties. This application is a divisional application of application Ser. No. 12/035,438, filed Feb. 22, 2008 (now abandoned), the contents of which are incorporated by reference in their entireties.

FIELD OF THE INVENTION

The invention is directed to a novel topical burn treatment compositions and their use in treating topical burns. These compositions may comprise a silicone containing compound, a Vitamin E compound and a local anesthetic.

BACKGROUND OF THE INVENTION

Skin burns result in dyskeratotic cells, spongiosis, vacuolation of keratinocytes and edema from capillary leakage. As a consequence, skin burns may be very painful. Furthermore, blisters may develop and scabs and scars may result.

One treatment that has been disclosed in U.S. Pat. No. 6,562,326 involves administering a composition comprising an anesthetic (e.g., tetracaine) and a surfactant (e.g., sodium lauryl sulfate).

Another treatment disclosed in EP 0446225B1 discloses the use of lidocaine to treat burns by systemic administration. There is a significant emphasis on treating internal injuries. There is no disclosure with respect to topical administration.

Jellish et al., 1999, Annals of Surgery 229:115-120 compares the effectiveness of lidocaine-prilocaine cream with bupivacaine. These preparations have been found to provide some relief.

Brofeldt et al., 1989, J. Burn Care Rehabil. 10:63-8 discloses the use of 5% lidocaine cream for the treatment of partial-thickness burns.

There is a need for a topical burn treatment composition that may relieve pain at the burn site and will facilitate healing of the skin at the burn site. It is an object of the invention to provide a composition for treatment of burns that will have an analgesic, anesthetic and repairing effect at the site of the burn.

SUMMARY OF THE INVENTION

The invention is directed to a topical composition comprising (a) a Vitamin E compound; (b) a silicone compound and (c) one or more anesthetics selected from the group consisting of esters, amides and ethers. In a particular embodiment the invention is directed to a) a Vitamin E compound; (b) a silicone oil and (c) lidocaine. In a more particular embodiment, the composition is an aqueous composition. In a most particular embodiment, the composition is a cream.

The invention is further directed to obtaining said composition. This method includes the following steps: combining a silicone compound and Vitamin E compound in an oleophilic system to obtain a first mixture and adding an aqueous solution of an anesthetic to said first mixture to obtain said composition.

The composition may further comprise a biological additive, which may include but is not limited to an aloe compound, *Arnica*, *Calendula* and/or *Chamomilla*. In one particular embodiment, the topical composition comprises: (a) a Vitamin E compound; (b) a silicone compound; (c) one or more anesthetics selected from the group consisting of esters, amides and ethers and (d) a biological additive. In a more particular embodiment, the topical composition comprises: (a) a Vitamin E compound; (b) a silicone oil; (c) lidocaine and (d) a biological additive that includes *Arnica*, but may also include aloe, *Calendula* and/or *Chamomilla*. This composition may be obtained by combining a silicone compound and Vitamin E compound in an water to obtain a first mixture and adding an aqueous solution of an anesthetic to said first mixture to obtain a third mixture and adding *Arnica* to said third mixture to obtain said composition. The composition may also further comprise an, an emollient, an emulsifier, a surfactant, a chelator, a biological additive, a dispersing agent, polyol, bisabolol and/or a pH stabilizing agent. In a particular embodiment, the composition of the present invention comprises a Vitamin E compound, polyol, an anesthetic, a silicone compound, a chelating agent, a bisabolol, a dispersing agent, an emulsifier, one or more emollients, a pH stabilizing agent and a biological additive. In a more particular embodiment, the composition comprises

TABLE I

| substance | % By Weight |
|---|---|
| Silicone compound | 0.1-10% |
| Vitamin E compound | 0.05-5% |
| Anesthetic | 0.5-10% |
| Biological additive(s) | 0.01-10 |
| Emulsifier(s) | 0.1-15 |
| Emollient(s) | 0.5-25 |
| Chelator | 0.02-2.0 |
| Dispersing agent | 0.05-5.0 |
| bisabolol | 0.0001-1.0 |
| Polyol | 0.1-10% |

This composition may be obtained using the following procedure:

(a) combining a polyol with a chelating agent, dispersing agent in water to obtain a first mixture;

(b) combining an emulsifier, emollient, a silicone compound, and Vitamin E compound to obtain a second mixture;

(c) adding the second mixture obtained in step (b) to the first mixture obtained in step (a) to obtain a third mixture;

(d) providing an aqueous solution of an anesthetic;

(e) adding the anesthetic of step (d) to the third mixture obtained in step (c) to obtain a fourth mixture;

(f) adding a biological additive and surfactant to the fourth mixture obtained in step (e) and (g) stabilizing the pH of the mixture obtained in step (f) to obtain said composition.

In an even more particular embodiment, the topical composition of the present invention comprises a Vitamin E compound, lidocaine, a silicone oil, one or more biological additives such as *Arnica* and optionally *Calendula*, *Chamomila* and/or an aloe compound, a surfactant, a chelating agent, a bisabolol, a dispersing agent, an emulsifier, one or more emollients, a pH stabilizing agent and a biological additive.

The topical compositions of the present invention may be used to treat burns, particularly skin burns in a subject. Thus the compounds in said composition are present in amounts effective to treat said burns. In a related aspect, the invention is directed to a method for treating a burn in a subject comprising topically administering to a subject in need thereof an amount of the composition effective to treat said burn. In a further related aspect, the invention is directed to the use of a silicone compound, Vitamin E compound, anesthetic and optionally surfactant, a chelating agent, a bisabolol, a dispersing agent, an emulsifier, one or more emollients, a pH stabilizing agent and a biological additive for the manufacture of a medicament for treating a minor burn in a subject.

DETAILED DESCRIPTION OF THE INVENTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As noted above, the compositions of the present invention are topical compositions and in a particular embodiment topical compositions for treating skin burns. As defined herein "treating skin burns" means modulating pain, inflammation, reddening, swelling of the skin, which may be accompanied by a rash or sores.

As noted above, the composition of the present invention comprises (a) a Vitamin E compound; (b) a silicone compound and (c) one or more anesthetics selected from the group consisting of esters, amides and ethers.

The Vitamin E compound includes but is not limited to tocopherol, a tocopherol ester such as tocopheryl acetate, tocopheryl succinate, tocopheryl nicotinate, tocopheryl linoleate or a mixture thereof. In a specific embodiment, the Vitamin E compound is tocopherol acetate. The Vitamin E compound may be present in an amount of about 0.05-5%, preferably about 0.1% to about 4%, more preferably about 0.5% to about 3%.

The silicone compound may in a particular embodiment may be a silicone oil. As defined herein "a silicone oil" includes but is not limited to water soluble or water insoluble volatile or non-volatile silicone oils. The term "volatile" means that the silicone has a measurable vapor pressure, i.e. a vapor pressure of at least 2 mm. of mercury at 20° C. If volatile, the silicone generally will have a viscosity of about 0.5 to 25 centistokes at 25° C. Suitable volatile silicones include cyclic silicones, linear silicones, or mixtures thereof. Examples of cyclic silicones include but are not limited to octamethylcyclotetrasiloxane, decamethylcyclopentasiloxane, hexamethyldisiloxane, cyclomethicone and mixtures thereof. The silicone may also be nonvolatile, and in particular water insoluble nonvolatile silicones. The term "nonvolatile" means that the silicone has a vapor pressure of less than 2 mm. of mercury at 20° C. A variety of silicones fit this definition including dimethicone, phenyl trimethicone, diphenyl dimethicone, hexadecyl methicone, stearoxydimethicone, stearyl dimethicone and cetyl dimethicone, silicone elastomers and polymers. In a particular embodiment, the silicone oil may be dimethicone and may also optionally include cyclomethicone. The silicone compound is present in an amount of 0.1-10%, preferably about 1% to about 8%, more preferable about 2% to about 7%. The anesthetic used in the compositions of the present invention is a topical anesthetic, which are esters, ethers or amides. Esters include but are not limited to tetracaine, benzocaine, proparacaine, procaine, and propoxycain. Amides include but are not limited to dibucaine and lidocaine. Ethers include but are not limited to dyclonine and promazine. In a specific embodiment, the anesthetic is lidocaine. The anesthetic is present in an amount of 0.5-10%, preferably about 1% to about 8%, more preferable about 1% to about 4%.

The composition may optionally further comprise a biological additive. which as defined herein as any compound obtained from a natural source, including but not limited to plants, animals, bacteria and yeast, which has a medicinal effect when applied to the skin. Examples include but are not limited to aloe compounds (e.g., aloe barbadensis and aloe vera in various forms such as juice and gel), *Arnica* (e.g., *Arnica montana*) (e.g., flower extract) in the form of either liquid or powder and *Chamomila* (e.g., in extract form), *Calendula* (e.g. in extract form) in liquid or extract form. The aloe generally comprises from 0.0001% to about 5.00%, preferably 0.001% to about 3.00%, more preferably about 0.05% to about 2.00% by weight of the composition of the present invention; *Arnica* generally comprises from about 0.0001% to about 5.00%, preferably 0.001% to about 3.00%, more preferably about 0.05% to about 2.00% by weight of the composition of the present invention; *Chamomila* comprises from about 0.0001% to about 5.00%, preferably from about 0.001% to about 3.00%, more preferably about 0.05% to about 2.00%; *Calendula* comprises from about 0.0001% to about 5.00%, preferably from about 0.001% to about 3.00%, more preferably about 0.05% to about 2.00% by weight of the composition of the present invention; The compositions of the present invention may further comprise bisabolol. Bisabolol may be synthetically produced or derived from chamomile and is commercially available from a variety of sources. Bisabolol generally comprises from 0.0001% to about 5.00%, preferably 0.005% to about 3.00%, more preferably about 0.02% to about 1.00%% by weight of the composition of the present invention.

The compositions of the present invention may further comprise one or more emulsifiers that are capable of forming an emulsion of the discontinuous and continuous phases. A wide variety of non-ionic or anionic emulsifiers of emulsifiers are useful herein and include but are not limited to sorbitan ester, glyceryl esters, polyglyceryl esters, methyl glucose esters, sucrose esters, ethoxylated fatty alcohols, hydrogenated castor oil ethoxylates, sorbitan ester ethoxylates, polymeric emulsifiers, soap systems and silicone emulsifiers. In a specific embodiment, the emulsifier may include but is not limited to cetearyl alcohol, stearyl alcohol, behentrimonium methosulfate cetearyl alcohol and/or behenyl alcohol. The emulsifier generally comprises from 0.1% to about 15%, preferably 1.0% to about 12%, more preferably about 2.0% to about 10% by weight of the composition of the present invention.

A further ingredient of the composition of the present invention is an emollient. As defined herein, an "emollient" is a material that protects against wetness or irritation, softens, soothes, supples, coats, lubricates, moisturizes, protects and/ or cleanses the skin. An example of an emollient includes but is not limited to a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and a hyaluronic acid compound or salt thereof. In a specific embodiment, the emollient is glycerin, pentylene glycol, dimethicone, cyclomethicone, cyclopentasiloxane polysilicone, caprylic/capric triglyceride, hyaluronic acid or salt thereof (e.g., sodium hyaluronate). The emollient generally comprises from 0.5% to about 25%, preferably about 2.0% to about 20%, more preferably about 5.0% to about 15.0% by weight of the composition of the present invention.

The composition may further comprise a chelating agent, such as EDTA or HEDTA. The chelator generally comprises from about 0.020% to about 2.0%, preferably about 0.05% to about 1.5%, more preferably about 0.1% to about 1.0% by weight of the composition of the present invention.

The cosmetic composition of the present invention is effective at pH values between pH 4 and pH 9. Preferably, the pH of the composition is between the following pH ranges: about 5.5 and about 6.5, about 4 to about 9, about 4 to about 8, about 4 to about 7, about 5 to about 9, about 5 to about 8, about 5 to about 7. Most preferably, the pH is about 6. One of ordinary skill in the art may add appropriate pH adjusting ingredients to the compositions of the present invention to adjust the pH to an acceptable range. One example of such a pH adjusting agent is an amino, such as triethanolamine NaOH, KOH.

The compositions of the present invention may be in the form of lotions, creams, gels, sticks, sprays, mousses, emollients, ointments and pastes. These product types may comprise several types of formulations including, but not limited to solutions, emulsions, gels, solids, and liposomes.

These formulations preferably contain a dispersing agent which includes but is not limited to magnesium aluminum silicate, Bentone Gels, cellulosic gums (e.g., cetyl hydroxyethylcellulose), beeswax (e.g., octyldodecanol beeswax). The dispersing agent generally comprises from about 0.1% to about 5.0%, preferably 0.2% to about 3.0%, more preferably about 0.5% to about 2.0% by weight of the composition of the present invention.

The use of such media and agents for dermatologically active substances is well known in the art. Except insofar as any conventional media or agent is incompatible with the active ingredient, its use in the therapeutic compositions is contemplated. Supplementary active ingredients can also be incorporated into the compositions.

The formulations further comprise a thickener. In a particular embodiment, the thickener is a cationic surfactant such as polyquaternium-37.

EXAMPLE

Example 1

One example of the composition of the present invention is shown in Table II

| NO. | PHASE | INCI DESIGNATION | WEIGHT |
|---|---|---|---|
| 1 | A | WATER (AQUA) | 50.74 |
| 2 | A | DISODIUM EDTA | 0.10 |

-continued

| NO. | PHASE | INCI DESIGNATION | WEIGHT |
|---|---|---|---|
| 3 | A | PENTYLENE GLYCOL | 3.00 |
| 4 | A | CETYL HYDROXYETHYLCELLULOSE | 0.25 |
| 5 | A | GLYCERIN | 1.35 |
| 6 | B | CETEARYL ALCOHOL CETEARETH-20 | 4.00 |
| 7 | B | DIMETHICONE | 0.50 |
| 8 | B | OCTYLDODECANOL BEESWAX | 0.50 |
| 9 | B | CYCLOPENTASILOXANE POLYSILICONE-11 | 1.00 |
|   | B | STEARYL ALCOHOL | 0.50 |
| 10 | B | #N/A | 5.00 |
| 11 | B | BEHENTRIMONIUM METHOSULFATE CETEARYL ALCOHOL | 4.00 |
| 12 | B | CAPRYLIC/CAPRIC TRIGLYCERIDE | 3.00 |
| 13 | B | BISABOLOL | 0.10 |
| 14 | B | TOCOPHERYL ACETATE | 2.00 |
|   | B | BEHENYL ALCOHOL | 0.50 |
| 15 | B | CAPRYLYL GLYCOL | 0.80 |
| 16 | C | LIDOCAINE HCL | 4.00 |
| 17 | C | WATER (AQUA) | 10.00 |
| 18 | D | ALOE VERA GEL | 1.00 |
| 19 | D | ARNICA MONTANA FLOWER EXTRACT ISI | 1.00 |
| 20 | D | CHAMOMILA RECUTITA (MATRICARIA) FLOWER EXTRACT ACTIVE ORGANICS | 0.50 |
| 21 | D | CALENDULA EXTRACT | 0.50 |
| 22 | D | SODIUM HYALURONATE | 2.00 |
| 23 | D | ETHYLHEXYL GLYCERIN | 1.00 |
| 24 | E | POLYQUATERNIUM-37 | 2.03 |
| 25 | E | 20% NAOH | 0.64 |

Phase "A" water is heated to 75° C. Natrasol, a thickening agent, is dispersed and is mixed with water for one hour. Remaining phase A ingredients are added. Phase B ingredients are combined and then mixed together at 75° C.; these ingredient are then mixed with Phase A ingredients to form (A+B). (A+B) is subsequently cooled to 30 C. Phase C ingredients are mixed together and then added to (A+B) to obtain (A+B+C). Phase D compounds are added one at a time. The pH is stabilized by adding NaOH.

Example 2

One example of the composition of the present invention is shown in Table II

| NO. | PHASE | INCI DESIGNATION | WEIGHT |
|---|---|---|---|
| 1 | A | WATER (AQUA) | 50.70 |
| 2 | A | DISODIUM EDTA | 0.10 |
| 3 | A | PENTYLENE GLYCOL | 3.00 |
| 4 | A | CETYL HYDROXYETHYLCELLULOSE | 0.25 |
| 5 | A | GLYCERIN | 1.35 |
| 6 | B | CETEARYL ALCOHOL CETEARETH-20 | 4.00 |
| 7 | B | DIMETHICONE | 0.50 |
| 8 | B | OCTYLDODECANOL BEESWAX | 0.50 |
| 9 | B | CYCLOPENTASILOXANE POLYSILICONE-11 | 1.00 |
| 10 | B | CROCADOL S95 | 0.50 |
| 11 | B | CYCLOPENTASILOXANE | 5.00 |
| 12 | B | BEHENTRIMONIUM METHOSULFATE CETEARYL ALCOHOL | 4.00 |
| 13 | B | CAPRYLIC/CAPRIC TRIGLYCERIDE | 3.00 |
| 14 | B | BISABOLOL | 0.10 |
| 15 | B | TOCOPHERYL ACETATE | 2.00 |
| 16 | B | BEHENYL ALCOHOL | 0.50 |
| 17 | B | CAPRYLYL GLYCOL | 0.80 |
| 18 | C | LIDOCAINE HCL | 4.00 |
| 19 | C | WATER (AQUA) | 10.00 |
| 20 | D | ALOE VERA GEL | 1.00 |

-continued

| NO. | PHASE | INCI DESIGNATION | WEIGHT |
|---|---|---|---|
| 21 | D | ARNICA MONTANA FLOWER EXTRACT ISI | 1.00 |
| 22 | D | CHAMOMILA RECUTITA (MATRICARIA) FLOWER EXTRACT ACTIVE ORGANICS | 0.50 |
| 23 | D | SODIUM HYALURONATE | 2.00 |
| 24 | D | ETHYLHEXYL GLYCERIN | 1.00 |
| 25 | E | POLYQUATERNIUM-37 | 2.03 |
| 26 | E | 20% NAOH | 1.18 |

Phase "A" water is heated to 75° C. Natrasol, a thickening agent, is dispersed and is mixed with water for one hour. Remaining phase A ingredients are added. Phase B ingredients are combined and then mixed together at 75° C.; these ingredient are then mixed with Phase A ingredients to form (A+B). (A+B) is subsequently cooled to 30 C. Phase C ingredients are mixed together and then added to (A+B) to obtain (A+B+C). Phase D compounds are added one at a time. The mixture is homogenized for two minutes at 3000 rpm.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for treating a burn in a subject in need thereof, comprising topically administering an effective amount of a topical emulsion composition comprising:
    a) 0.5-5 wt. % of a Vitamin E compound;
    b) 0.1-10 wt. % of a silicone oil compound, comprising cyclopentasiloxane, polysilicone-11, or dimethicone;
    c) 0.5-10 wt. % of lidocaine; and
    d) a biological additive comprising aloe compounds, *Arnica*, chamomile, or *Calendula*.

2. The method of claim 1, wherein the topical emulsion composition is in the form of an ointment or cream.

3. The method of claim 1, wherein the topical emulsion composition is an aqueous emulsion composition.

4. The method of claim 1, wherein the topical emulsion composition further comprises an emulsifier, an emollient, a chelating agent, a dispersing agent, bisabolol, a polyol, a surfactant, or a pH stabilizing agent.

5. The method of claim 4, wherein the topical emulsion composition comprises 0.5-3 wt. % of the Vitamin E compound.

6. The method of claim 5, wherein the topical emulsion composition comprises 2-7 wt. % of the silicone oil compound, comprising cyclopentasiloxane, polysilicone-11, or dimethicone.

7. The method of claim 6, wherein the topical emulsion composition comprises 1-8 wt. % of lidocaine.

8. The method of claim 7, wherein the topical emulsion composition comprises 0.01-10 wt. % of the biological additive comprising aloe compounds, *Arnica*, chamomile, or *Calendula*.

9. The method of claim 8, wherein the topical emulsion composition comprises aloe compounds and chamomile.

10. The method of claim 9, wherein the topical emulsion composition further comprises *Arnica*.

11. The method of claim 10, wherein the topical emulsion composition comprises 1-4 wt. % of lidocaine.

12. The method of claim 10, wherein the topical emulsion composition further comprises 0.1-15 wt. % of an emulsifier.

13. The method of claim 10, wherein the topical emulsion composition further comprises 0.5-25 wt. % of an emoillient.

14. The method of claim 10, wherein the topical emulsion composition further comprises 0.2-2 wt. % of a chelating agent.

15. The method of claim 10, wherein the topical emulsion composition further comprises 0.05-5 wt. % of a dispersing agent.

16. The method of claim 10, wherein the topical emulsion composition further comprises 0.0001-1 wt. % of bisabolol.

17. The method of claim 10, wherein the topical emulsion composition further comprises 0.1-10 wt. % of a polyol.

18. The method of claim 10, wherein the topical emulsion composition further comprises a thickener comprising a cationic surfactant.

19. The method of claim 10, wherein the topical emulsion composition is in the form of an ointment or cream.

20. The method of claim 10, wherein the topical emulsion composition is an aqueous emulsion composition.

* * * * *